(12) United States Patent
Elson et al.

(10) Patent No.: US 7,691,830 B2
(45) Date of Patent: Apr. 6, 2010

(54) METHOD AND COMPOSITION FOR TREATMENT OF A MUCOSAL TISSUE DISORDER

(76) Inventors: Clive Elson, 66 Braemount Drive, Halifax, Nova Scotia (CA) BMB 3PC; Agis Kydonieus, 17 Savage Rd., Kendell Park, NJ (US) 08824; Susan Elizabeth Henderson, 19 Belmore Dr., Wellington, Nova Scotia (CA) B2T 1J4

( * ) Notice: Subject to any disclaimer, the term of this patent is extended or adjusted under 35 U.S.C. 154(b) by 0 days.

(21) Appl. No.: 11/059,943

(22) Filed: Feb. 17, 2005

(65) Prior Publication Data

US 2006/0183711 A1 Aug. 17, 2006

(51) Int. Cl.
*A61K 31/737* (2006.01)
(52) U.S. Cl. .......................................... 514/55; 514/538
(58) Field of Classification Search ................... 514/55, 514/538
See application file for complete search history.

(56) References Cited

U.S. PATENT DOCUMENTS 5,563,130 A * 10/1996 Backer et al. ............... 514/152
2003/0161884 A1 * 8/2003 Rosenberg et al. ........... 424/486

FOREIGN PATENT DOCUMENTS

WO WO2004/018010 A2 3/2004

OTHER PUBLICATIONS

Goodman and Gilman's "The Pharmacological Basis of Therapeutics", 10th Ed., 1996, p. 54-57.*
Trisha Gura, Science, Nov. 1997, 278(5340), 1041-1042.*
Tokura et J.M.S. Pure Applied Chemistry, 1994, A31(11), 1701-1708.*
The Merck Manual, 16th Ed., 1992, pp. 830-834; 841-845 and p. 1722.*
Tiyaboonchai, Naresuan University Journal, 2003, 11(3), 51-56.*
Wood et al Drug Therapy, Mar. 28, 1995, 841-848.*
Berge, et al., "Pharmaceutial Salts", Journal of Pharmaceutical Sciences (1977), V. 66, pp. 1-19.
Fleischmann, et al., "Clinical and Immunological Response to Nifedipine for the Treatment of Interstitial Cystitis", Journal of Urology (1991), V. 146, pp. 1235-1239.
Hirano, et al., "Effect of Sulfated Derivatives of Chitosan on some Blood Coagulant Factors", Carbohydrate Research (1985), V. 137, pp. 205-215.
Messing, et al., "Interstitial Cystitis: Early Diagnosis, Pathology, and Treatment", Urology (1978), V. 12, No. 4, pp. 381-392.
Stewart, et al., "The Use of Dimethyl Sulfoxide (DMSO) in the Treatment of Interstitial Cystitis", Journal of Urology (1968), V. 98, pp. 671-672.
Tokura, et al., "Selective Sulfation of Chitin Derivatives for Biomedical Functions", J.M.S-Pure and Applied Chemistry (1994), V. A31 (11), pp. 1701-1718.
Whistler, et al., "Anticoagulant Activity of Oxidized and N- and O-Sulfated Chitosan", Archives of Biochemistry and Biophysics (1971), V. 142, pp. 106-110.
Hanno, et al., "Conservative Therapy of Interstitial Cystitis", Seminars in Urology (1991), V. 9, No. 2, pp. 143-147.

* cited by examiner

*Primary Examiner*—Shaojia Anna Jiang
*Assistant Examiner*—Ganapathy Krishnan
(74) *Attorney, Agent, or Firm*—Edwards Angell Palmer & Dodge LLP; Ralph A. Loren; Amy DeCloux

(57) ABSTRACT

Methods of treating a subject suffering from a disorder in a mucosal tissue, such as interstitial cystitis; cancer in a mucous membrane such as bladder or vaginal cancer; Crohn's disease; inflammatory bowel disease or colitis, by administering a medicament containing a sulfated chitinous polymer administered topically are described. Pharmaceutical compositions containing the sulfate chitinous polymer are also disclosed.

14 Claims, 1 Drawing Sheet

TNF levels in the urine of the treatment groups

METHOD AND COMPOSITION FOR TREATMENT OF A MUCOSAL TISSUE DISORDER

BACKGROUND OF THE INVENTION

Many disease states lead to disorders of mucosal membranes. One of the more common mucosal membrane disorders is interstitial cystitis. Interstitial cystitis is a poorly understood bladder condition for which there is no universal effective treatment program (Fleischmann, J. D. et al. 1991. *J. Urology*, 146:1235). Symptoms include urgency for urination, increased frequency of urination and suprapubic pain usually relieved by voiding. Other symptoms include arthritis, spastic colon and low grade fever. Individuals with interstitial cystitis can be significantly disabled, and individuals with advanced interstitial cystitis can require major surgery in order to function.

There is no standard treatment for interstitial cystitis. Among the treatments used are hydraulic distention of the bladder, oral amitriptyline or sodium pentosanpolysulfate, intravesical instillation of dimethylsulfoxide, oxychlorosene sodium, silver nitrate, heparin, or of a composition comprising an angiostatic steroid and pentosanpolysulfate. However, both the efficacy and the effectiveness of these treatments is variable.

Hydraulic distention of the bladder is done under general or spinal anesthesia for one to two minutes at a pressure of 80 to 100 cm $H_2O$. In one study using hydraulic distention of the bladder to treat interstitial cystitis, less than 55% of the patients treated reported relief immediately after treatment and only 2% reported relief six months after treatment (Hanno P. M. et al. 1991. *Semin Urology*, 9:143).

Instillation of dimethylsulfoxide (DMSO) into the bladder for six to eight weeks resulted in a 53% response rate to DMSO versus an 18% response rate to placebo, with the average length of response being six months (Perez-Marrero, R. et al. 1967. *J. Urology*, 98: 671). Pharmacological effects of DMSO include membrane penetration, enhanced drug absorption, anti-inflammatory and analgesic effects, collagen dissolution, muscle relaxation and mast cell histamine release. Side effects include increased vesicle irritability and garlic-like breath odor.

Equivalent results to instillation of DMSO have been reported with oxychlorosene sodium (Messing, E. M. et al. 1978. *Urology*, 12:381). However, instillation of oxychlorosene sodium requires anesthesia because of intense discomfort.

While interstitial cystitis is an important disorder that may cause disruption or irritation of the mucosal membranes, other conditions, such as colitis, Crohn's disease and even some forms of cancer, such as bladder cancer, also appear to cause similar problems.

Therefore, there is a need for a therapeutic agent for the treatment of interstitial cystitis and other conditions which affect the mucosal membranes with improved efficacy, without major surgery, undesirable side effects, or intense physical discomfort.

Accordingly, it is an object of the present invention to provide a method for treating a disorder of a mucosal membrane such as bladder cancer, Crohn's disease or colitis, lung cancer, pulmonary and respiratory diseases, gynecological malignancies and cancer of the mouth.

Another object of the invention is to provide a method for treating a subject suffering from interstitial cystitis.

It is also an object of the invention to provide a pharmaceutical composition acceptable for administration via, for example, catheter or enema.

A further object of the invention is to provide novel sulfated chitinous polymers.

These and other objects, features, and advantages of the invention will be apparent from the following description and claims.

SUMMARY OF THE INVENTION

The present invention provides a method for the treatment of a disorder in a mucosal membrane, such as cancer (e.g. carcinomas, sarcomas, etc.) of a mucosal tissue, by administering a medicament containing a sulfated chitinous polymer to a subject in need thereof. Examples of disorders that can be treated by the present invention include, but are not limited to, bladder, colon and prostate cancers and disorders; urinary tract disorders; Crohn's disease; colitis; irritable and inflammatory bowel diseases; vaginal and gynecological cancers; stomach, abdominal and intestinal cancers; lung cancer and pulmonary/respiratory diseases, such as cystic fibrosis; mouth, buccal and oral cancer and diseases; breast cancer and squamous cell carcinomas.

The present invention also provides a method for treating interstitial cystitis in a subject such as a human patient by topically administering an effective amount of a medicament containing a sulfated chitinous polymer to the affected areas of the subject. A medicament containing the sulfated chitinous polymer can be administered in combination with another drug or active agent, particularly after a surgical procedure to treat, for example, colon, prostate, gynecological, breast, stomach, abdominal or lung cancer.

The invention further provides a pharmaceutical composition acceptable for, but is not limited to, administration via catheter or an enema. The pharmaceutical composition contains an effective amount of a sulfated chitinous polymer and a pharmaceutically acceptable carrier.

The methods of the invention use sulfated chitinous polymers that include subunits of the formula:

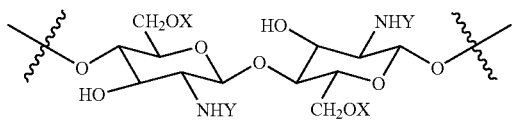

wherein

X is independently selected from hydrogen, $SO_3^-B$, $—(CH_2)_bCOG$, or $—(CH_2)_bCOOZ$ for each occurrence;

Y is independently selected from $SO_3^-B$, $—C(=O)—R—CO_2Z$, $—C(=O)—R—COG$, hydrogen, carboxyalkyl, acetyl, or a pharmaceutically acceptable salt thereof for each occurrence, provided that at least 1% of Y and/or X groups on said polymer are $SO_3^-B$ and that at least 1% of Y groups on said polymer are $—C(=O)—R—CO_2Z$ or $—C(=O)—R—COG$;

R is independently selected from the group consisting of alkyl, alkenyl, and aryl;

b is 1-5;

B is hydrogen or a cation;

G is an additional therapeutic agent or a pharmaceutically acceptable salt thereof; and Z is hydrogen, a cation, an additional therapeutic agent, or a pharmaceutically acceptable salt thereof.

Preferably, at least 10% of X groups on said polymer are —$(CH_2)_b$COOZ or —$(CH_2)_b$COG.

The invention also provides novel sulfated chitinous polymers.

DETAILED DESCRIPTION OF THE INVENTION

Figure 1:
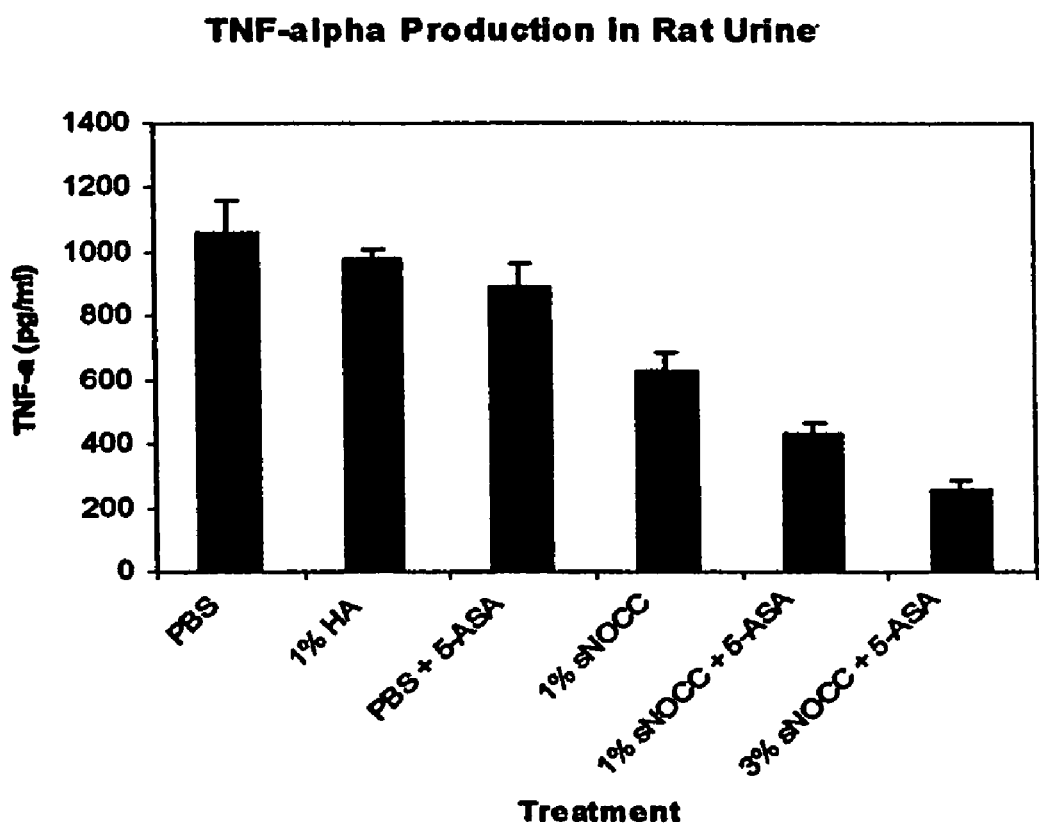
FIG. 1 is a bar graph that shows the results of assessment of TNF levels in the urine of the rats in the different treatment groups of Example 1.

Interstitial cystitis (IC) is a chronic debilitating disease that causes urgent and sometimes painful urination as well as diffuse pelvic pain. The etiology is uncertain but there is evidence that it may be autoimmune in nature. The initiating event may be bacterial or viral infection in the bladder. At a histological level, IC is characterized by inflammation and the influx of inflammatory cells such as neutrophils, macrophages and mast cells into the bladder interstitia.

The invention provides a method for treating a subject suffering from interstitial cystitis. The method includes the topical administration of an effective amount of a medicament containing a sulfated chitinous polymer to the affected areas of the subject. The medicament can be administered in combination with another drug or active agent, particularly after a surgical operation for the treatment of diseases after the operation.

The present invention further provides a method of treatment of a disorder in a mucosal tissue, such as a mucosal membrane, and/or an epithelial tissue. The present invention has particular applicability to the treatment of mucosal tissue disorders of the urinary tract of a mammalian, preferably human, subject.

Examples of disorders in mucosal membranes or mucosal tissue include, but are not limited to, colitis, such as ulcerative colitis, granulomatous colitis, ischemic colitis, radiation colitis, pseudomembranous colitis and bacillary or amebic dysentery; Crohn's disease and other disorders of the colon and ileum; gastrointestinal disorders such as irritable bowel syndrome including spastic colon and mucous colitis; urinary bladder disorders, such as transitional cell carcinoma, squamous cell carcinoma and adenocarcinoma of the bladder; multiple endocrine neoplasia; thyroid carcinoma; gynecologic malignancies as in endometrial and vaginal cancer, e.g.; carcinomas and sarcomas; mucosal sarcomas such as Karposi's sarcomas; ear, nasopharyngeal and oralmucosal carcinomas including cancer of the mouth; lung cancer and pulmonary and respiratory diseases.

Examples of squamous cell carcinomas of the mucosal membranes that can be treated by the present method include, but are not limited to, carcinomas of the head and neck (including mouth, tongue, tonsil, nasopharynx, oropharynx, sinus, palate, lip, buccal mucosa, gingivae, epiglottis, skin and larynx), tympanic secretory glands, gastrointestinal, urinary tract, vagina, penis, cervix and vulva.

The following definitions are used throughout the specification.

The term "topical administration" or "topically administering" includes, but is not limited to, administering directly to surfaces in the body (e.g., delivery to vagina, mouth, ear, or eye); via catheter; via enema; and/or via spray to surfaces within the body (e.g., delivery to the bladder, rectum, lung, oral or nasal mucosal surfaces).

The term "affected areas" include mucosal tissue, such as mucosal membranes, epithelial tissue, and the external and/or the internal surfaces of these, such as the internal surface of the bladder and associated structures such as the ureters and urethra. It also includes any other portions of the subject to which the administration of the composition of the invention would be beneficial to the subject, e.g., internal areas, external areas, rectal area, colon area, etc.

The term "subject" includes organisms which are capable of suffering from interstitial cystitis and who would benefit from the methods and compositions of the invention. Examples of subjects include mammals such as dogs, cats, horses, mice, rats, rabbits, and, preferably, humans.

The term "sulfated chitinous polymers" includes sulfated derivatives of chitin, chitosan, and other chitinous polymers. Examples of chitinous polymers include those described in, for example, Hayes U.S. Pat. No. 4,619,995; Tokura et al. *J.M.S.—Pure Appl. Chem.* A31(11), pp. 1701-1718 (1994); Hirano et al. *Carbohydrate Research,* 137 (1985) p. 205-215; and Whistler et al. *Archives Biochem. Biophys.* 142 (1971) p. 106-110, hereby incorporated herein by reference in their entirety. Examples of sulfated chitinous polymers N-sulfated-N,O-carboxyalkylchitosan (e.g., N-sulfated-N,O-carboxymethylchitosan, N-sulfated-N,O-carboxyethylchitosan, and N-sulfated-N,O-carboxypropylchitosan), N-sulfated O-carboxyalkylchitosan (N-sulfated O-carboxymethylchitosan, N-sulfated O-carboxyethylchitosan, and N-sulfated O-carboxypropylchitosan), and sulfated chitosan. Sulfated chitinous polymers are also described in WO 2004/018010, incorporated herein by reference.

The sulfated chitinous polymers useful in the methods of the invention include polymers that are comprised of subunits of the formula:

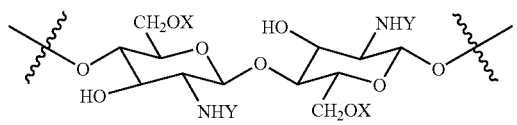

wherein

X is independently selected from hydrogen, $SO_3^-B$, —$(CH_2)_b$COG, or —$(CH_2)_b$COOZ for each occurrence;

Y is independently selected from $SO_3^-B$, —C(=O)—R—$CO_2Z$, —C(=O)—R—COG, hydrogen, carboxyalkyl, acetyl, or a pharmaceutically acceptable salt thereof for each occurrence, provided that at least 1% of Y groups and/or 1% of X groups on said polymer are $SO_3^-B$;

R is independently selected from the group consisting of alkyl, alkenyl, and aryl;

b is 1-5;

B is hydrogen or a cation;

G is an additional therapeutic agent or a pharmaceutically acceptable salt thereof; and Z is hydrogen, a cation, an additional therapeutic agent, or a pharmaceutically acceptable salt thereof.

Preferably, at least 10% of X groups on said polymer are —$(CH_2)_b$COOZ or —$(CH_2)_b$COG.

The sulfated chitinous polymers of the invention have at least 1%, but possibly 15%, 20%, 25%, 30%, 40%, 50%, 60%, or 70% of the Y and/or X groups of the polymer are $SO_3^-B$. Advantageously, b may be 1, 2, or 3.

Examples of cations include sodium, potassium, calcium, magnesium, etc.

The sulfated chitinous polymers of the invention may be water soluble at acidic, neutral, and/or basic pH's. Advantageously, the polymers may be water soluble at pH's ranging from about 1 to about 11.

Idealized structures of each of these sulfated chitinous polymers are shown below. These structures are not meant to be limiting, with respect to the derivatization of the chitinous polymer. One of skill in the art will appreciate that the derivatization pattern of the polymers and/or the particular salt can be varied, as appropriate.

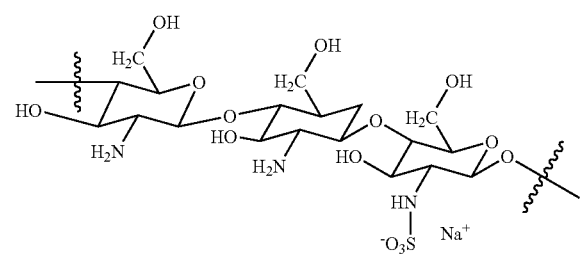

Sulfated Chitosan (S-SAN)

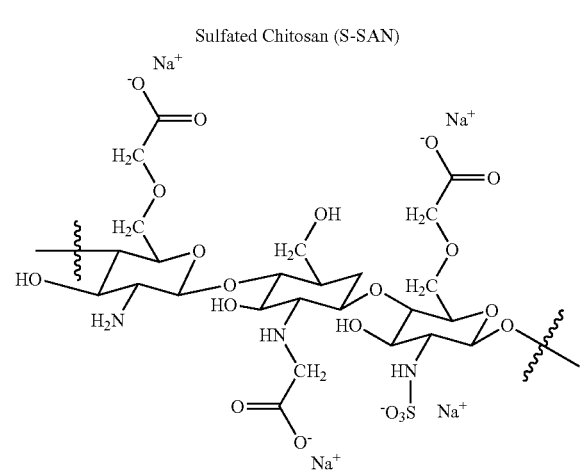

N-Sulfated N, O-Carboxymethyl Chitosan (S-NOCC)

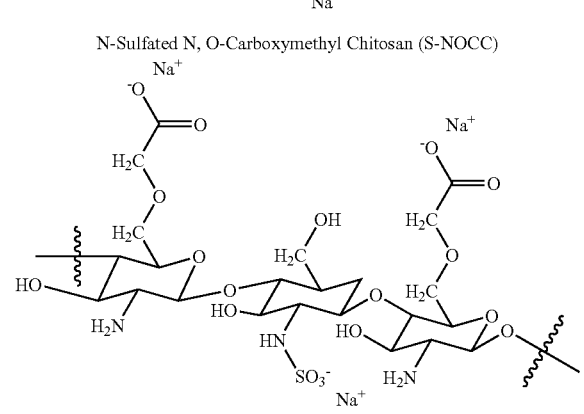

N-Sulfated O-Carboxymethyl Chitosan (S-OCC)

The sulfated chitinous polymers may be synthesized by using methods known in the art. For example, generally, NOCC has about 30-70% of the total nitrogen centers on the polymer in the form of amines. The amines may then react with a sulfur trioxide-pyridine reagent at room temperature and basic pH to form $NHSO_3^-$ groups along the polymer. The oxygen centers in chitosan and its derivatives can also be sulfated under anhydrous conditions using dimethylformamide-sulfur trioxide reagents. It is expected that O-sulfated or N,O-sulfated chitinous materials will also perform in accordance with the teachings of this invention. Methods of synthesizing N-acylated chitinous polymers are described in U.S. patent application Ser. No. 10/810,742.

An additional therapeutic agent may also be administered as a part of the medicament, e.g., covalently or ionically bound to the sulfated chitinous polymer (e.g., as G or Z).

The additional therapeutic agent may also be administered in combination with the sulfated chitinous polymer. The therapeutic agent may be dispersed within the chitinous polymer, but not necessarily covalently bound to it.

Examples of additional therapeutic agents include agents which may benefit the subject or treat, at least in part, one or more symptoms of interstitial cystitis. For examples, the additional agent can be an agent which is known to be of benefit to interstitial cystitis patients, such as 5-aminosalicylic acid (5-ASA), pentosan polysulfate, hydrocortisone, DMSO, heparin, silver nitrate, sodium oxychlorosene, Bacille Calmette-Guérin (BCG), or combinations thereof.

Other additional therapeutic agents which may be administered in combination with the sulfated chitinous polymers of the invention include antibiotic, anesthetic, antifungal, antiparasitic, cancer and antiinflammatory agents. Anticancer agents include, but are not limited to, trastuzumab (HERCEPTIN®), paclitaxel (TAXOL®), docetaxel (TAXOTERE®), capecitabine (XELODA®), carboplatin (PARAPLATIN®), (ANGIOSTATINV®), (ENDOSTATIN®) & other anti-angiogenesis drugs, exisulind (APTOSYN®), pemetrexed (ALIMTA®), ibandronate (BONDRONAT®), imatinib (GLEEVEC®), gefitinib (IRESSA®), doxorubicin HCl (DOXIL®), topotecan (HYCAMTIN®), cisplatin (PLATINOL®), rituximab, thalidomide (RITUXAN®), bevacizumab, rhuMAb-VEGF AVASTIN™, oxaliplatin (ELOXATIN®), IMC-C225, cetuximab (ERBITUX®), gemcitabine, 5-fluorouracil (GEMZAR®), irinotecan (CAMPTO®), vinorelbine, satraplatin, valorubicin (NAVELBINE®) or combinations thereof.

Examples of antibiotics include chemical substances that inhibits the growth of, or kills, microorganisms. Antibiotics include, but are not limited to, penicillin, tetracyclines, clarithromycin (BIAXIN®), ciprofloxacin (CIPRO®), and metronidazole (FLAGYL®).

The term "antifungal agent" includes agents which are known in the art to have fungistatic or fungicidal activity. Examples of antifungal agents include, but are not limited to, azoles (e.g., fluconazole, itraconazole, ketoconazole, miconazole, clortrimazole, voriconazole, posaconazole, rovuconazole, etc.), polyenes (e.g., natamycin, lucensomycin, nystatin, amphotericin B, etc.), echinocandins (e.g., CANCIDAS®), pradimicins (e.g., beanomicins, nikkomycins, sordarins, allylamines, etc.) and derivatives and analogs thereof.

Examples of antiinflammatory agents include non-steroidal anti-inflammatory drug(s) (NSAIDs), cytokine suppressive anti-inflammatory drug(s) (CSAIDs), MK-966 (COX-2 Inhibitor), iloprost, methotrexate, thalidomide and thalidomide-related drugs (e.g., CELGEN), leflunomide, tranexamic acid, T-614, prostaglandin E1, tenidap, naproxen, meloxicam, ibuprofen, piroxicam, diclofenac, indomethacin, sulfasalazine, azathioprine, ICE inhibitors (inhibitors of the enzyme interleukin-1β converting enzyme), zap-70 and/or lck inhibitors (inhibitor of the tyrosine kinase zap-70 or lck), corticosteroid anti-inflammatory drugs (e.g., SB203580), TNF-convertase inhibitors, interleukin-17 inhibitors, gold, penicillamine, chloroquine, hydroxychloroquine, chlorambucil, cyclophosphamide, cyclosporine, total lymphoid irradiation, anti-thymocyte globulin, CD5-toxins, lobenzarit disodium, cytokine regulating agents (CRAs) HP228 and HP466, prednisone, orgotein, glycosaminoglycan polysulfate, minocycline, anti-IL2R antibodies, auranofin, phenylbutazone, meclofenamic acid, flufenamic acid, intravenous immune globulin, zileuton, mycophenolic acid (RS-61443), tacrolimus (FK-506), sirolimus (rapamycin), amiprilose (therafectin), cladribine (2-chlorodeoxyadenosine), azaribine, and methotrexate.

Examples of anesthetic agents include as phenol, benzyl benzoate, calamine, chloroxylenol, dyclonine, ketamine, menthol, pramoxine, resorcinol, troclosan, benzocaine, bupivacaine, chloroprocaine, cinchocaine, dexivacaine, diamocaine, dibucaine, etidocaine, hexylcaine, levobupivacaine, lidocaine, mepivacaine, oxethazaine, prilocaine, procaine, proparacaine, propoxycaine, pyrrocaine, risocaine, rodocaine, ropivacaine, and tetracaine; and pharmaceutically acceptable derivatives thereof, and combinations thereof.

The term "alkyl," as used herein, includes saturated aliphatic groups, including straight-chain alkyl groups (e.g., methyl, ethyl, propyl, butyl, pentyl, hexyl, heptyl, octyl, nonyl or decyl), branched-chain alkyl groups (e.g., isopropyl, tert-butyl or isobutyl,), and cycloalkyl (alicyclic) groups (e.g., cyclopropyl, cyclopentyl, cyclohexyl, cycloheptyl, or cyclooctyl). The term alkyl further includes molecules having oxygen, nitrogen, sulfur or phosphorous atoms replacing one or more carbons of the hydrocarbon backbone. Preferably, a straight chain or branched chain alkyl with 10 or fewer carbon atoms in its backbone (e.g., $C_1$-$C_{10}$ for straight chain, $C_3$-$C_{10}$ for branched chain) is used, and, more preferably, 4 or fewer. Cycloalkyls may have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carboxylate, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), cyano, azido, nitro, or an aromatic or heteroaromatic moiety.

The term "aryl" includes groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. The aromatic ring can be substituted at one or more ring positions with such substituents as described above, as for example, halogen, hydroxyl, alkoxy, carboxylate, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, alkylthio, nitro, cyano, or azido.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl or decenyl), branched-chain alkenyl groups and cycloalkenyl (alicyclic) groups (cyclopropenyl, cyclopentenyl, cyclohexenyl, cycloheptenyl or cyclooctenyl) groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group with 10 or fewer carbon atoms in its backbone (e.g., $C_2$-$C_{10}$ for straight chain, $C_3$-$C_{10}$ for branched chain) is used. Likewise, cycloalkenyl groups may have from 3-8 carbon atoms in their ring structure, and more preferably have 5 or 6 carbons in the ring structure. The term $C_2$-$C_{10}$ includes alkenyl groups containing 2 to 10 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, halogen, hydroxyl, carboxylate, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), cyano, azido, nitro, or an aromatic or heteroaromatic moiety.

The term "carboxyalkyl" includes carboxyl groups covalently bonded to an alkyl, alkenyl, or aryl group. The carboxyl group may be, for example, of the formula: —$(CH_2)_c$COOZ, wherein c is 1-8, and Z is as defined above. Examples of carboxyalkyl groups include carboxymethyl, carboxyethyl, carboxypropyl, and the like.

The invention also pertains, at least in part, to all novel sulfated chitinous polymers described herein. These sulfated chitinous polymers include polymers comprised of subunits of the formula:

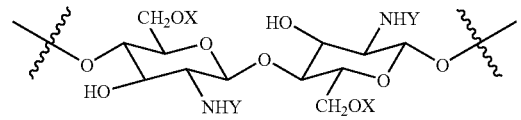

wherein

X is independently selected from hydrogen, $SO_3^-B$, —$(CH_2)_b$COG or —$(CH_2)_b$COOZ for each occurrence, provided that at least 10% of X groups on said polymer are —$(CH_2)_b$COOZ or —$(CH_2)_b$COG;

Y is independently selected from $SO_3^-B$, —C(=O)—R—$CO_2Z$, —C(=O)—R—COG, hydrogen, carboxyalkyl, acetyl, or a pharmaceutically acceptable salt thereof for each occurrence, provided that at least 1% of Y and/or X groups on said polymer are $SO_3^-B$ and that at least 1% of Y groups on said polymer are —C(=O)—R—$CO_2Z$ or —C(=O)—R—COG;

R is independently selected from the group consisting of alkyl, alkenyl, and aryl;

b is 1-5;

B is hydrogen or a cation;

G is an additional therapeutic agent or a pharmaceutically acceptable salt thereof; and Z is hydrogen, a cation, an additional therapeutic agent, or a pharmaceutically acceptable salt thereof.

The sulfated N-acylated chitinous polymers of the invention have at least 5%, but possibly 15%, 20%, 25%, 30%, 40%, 50%, 60%, or 70% of the X groups of the polymer are of the formula —$(CH_2)_b$COOZ or —$(CH_2)_b$COG.

In addition, the N-acylated chitinous polymers have at least 1%, but possibly 2.5%, 5%, 7.5%, 10%, 12.5%, 15%, 17.5%, 20%, 25%, 30%, 35% or 40% of the Y groups on the polymer are —C(=O)—R—CO$_2$Z or —C(=O)—R—COG. R has the formula —(CH$_2$)$_a$—, wherein a is between 1-8. Advantageously, a may be 2, 3 or 4. R can also be aryl (e.g., phenyl, naphthyl, heteroaryl, etc.), alkyl or alkenyl. R may also comprise one or more heteroatoms replacing one or more carbons of the alkyl or alkenyl group.

Examples of polymers of the invention include sulfated N,O-carboxymethyl-N-succinylchitosan, sulfated N,O-carboxymethyl-N-citraconylchitosan, sulfated N,O-carboxymethyl-N-glutarylchitosan, and mixtures thereof.

The invention also includes methods of administering the sulfated chitinous polymer in combination with a pharmaceutically acceptable carrier. The pharmaceutically acceptable carrier may be selected such that it is suitable for administration via catheter or enema.

The invention also provides a pharmaceutical composition acceptable for administration via catheter and/or an enema. The compositions comprise an effective amount of a sulfated chitinous polymer and a pharmaceutically acceptable carrier. The sulfated chitinous polymer can be administered in an embodiment at a concentration of about 0.5% to about 30%, or, in one embodiment, preferably 1.0% to about 10% of the total weight of the composition.

The pharmaceutically acceptable carrier may include a pharmaceutically acceptable material, composition or vehicle, such as a liquid or solid filler, diluent, excipient, solvent or encapsulating material, involved in carrying or transporting the therapeutic composition of the invention, e.g., a sulfated chitinous polymer, within or to the subject such that the composition can perform its intended function, e.g., treat interstitial cystitis. Such compositions are generally carried or transported from one organ, or portion of the body, to another organ, or portion of the body. Each additional carrier must be "acceptable" in the sense of being compatible with the other ingredients of the formulation and not injurious to the subject. Some examples of materials which can serve as additional pharmaceutically acceptable carriers include: water; sugars such as lactose, glucose and sucrose; starches such as corn starch and potato starch; cellulose, and its derivatives, such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; stabilizers; antioxidants such as, EDTA and metabisulfite; and other non-toxic compatible substances employed in pharmaceutical formulations.

The sulfated chitinous polymers generally contain basic functional groups, such as amino groups, and are, thus, capable of forming pharmaceutically acceptable salts with pharmaceutically acceptable acids or anions. The term "pharmaceutically acceptable salts" in this respect, refers to the relatively non-toxic, inorganic and organic acid addition salts of compounds of the invention. These salts can be prepared in situ during the final isolation and purification of the compounds of the invention, or by separately reacting a purified compound of the invention in its free base form with a suitable organic or inorganic acid, and isolating the salt thus formed. Representative salts include hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulfonate salts and the like. (See, e.g., Berge et al. (1977) "Pharmaceutical Salts", *J. Pharm. Sci.* 66:1-19).

The sulfated chitinous polymers may also contain one or more acidic functional groups and, thus, are capable of forming pharmaceutically acceptable salts with pharmaceutically acceptable bases or cations. The term "pharmaceutically acceptable salts" in these instances refers to the relatively non-toxic, inorganic and organic base addition salts of compounds of the invention. These salts can likewise be prepared in situ during the final isolation and purification of the compounds, or by separately reacting the purified compound in its free acid form with a suitable base, such as hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the composition of the invention.

Formulations of the invention include those suitable for topical (includes administration to the internal surfaces of the bladder, ureters, and urethra) and/or rectal administration. The formulations may conveniently be presented in unit dosage form and may be prepared by any methods well known in the art of pharmacy. The formulations may include, but are not limited to, the sulfated chitinous polymer, and a pharmaceutically acceptable carrier.

Suspensions, in addition to sulfated chitinous polymer, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the therapeutic agent and sulfated chitinous polymer for rectal administration may be presented as a suppository, which may be prepared by mixing the therapeutic agent and the sulfated chitinous polymer with one or more suitable nonirritating excipients or carriers comprising, for example, cocoa butter, polyethylene glycol, a suppository wax or a salicylate, and which is solid at room temperature, but liquid at body temperature and, therefore, will melt in the rectum and release the sulfated chitinous polymer.

Dosage forms for the topical administration of the sulfated chitinous polymer of this invention include powders, sprays, ointments, pastes, creams, lotions, gels, solutions, and patches. Powders and sprays that are used for the delivery of substances to the nasal and lung mucosal tissues can be particularly useful in the present invention. The sulfated chitinous polymer may be mixed under sterile conditions with a pharmaceutically acceptable carrier, and with any preservatives, buffers, or propellants that may be required.

The ointments, pastes, creams and gels may contain, in addition to the therapeutic agent and sulfated chitinous polymer, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions may also contain adjuvants such as preservatives, wetting agents, emulsifying agents and dispersing agents. Prevention of the action of microorganisms may be ensured by the inclusion of various antibacterial, anticancer and antifungal agents, for example, paraben, chlorobutanol, phenol sorbic acid, and the like. It may also be desirable to include isotonic agents, such as sugars, sodium chloride, and the like into the compositions.

The language "effective amount" of the polymer or agent is that amount necessary or sufficient to treat or prevent interstitial cystitis in a subject, e.g., prevent the various morphological and somatic symptoms of the particular disorder. The effective amount can vary depending on such factors as the size and weight of the subject, the type of disorder, or the particular polymer and/or agent. For example, the choice of the polymer and/or agent can affect what constitutes an "effective amount". One of ordinary skill in the art would be able to study the aforementioned factors and make the determination regarding the effective amount of without undue experimentation.

The regimen of administration can affect what constitutes an effective amount. The polymer and/or agent can be administered to the subject either prior to or after the onset of interstitial cystitis. Further, several divided dosages, as well as staggered dosages, can be administered daily or sequentially, or the dose can be continuously infused. Further, the dosages of the polymers and/or agents can be proportionally increased or decreased as indicated by the exigencies of the therapeutic or prophylactic situation.

The term "treated," "treating" or "treatment" includes therapeutic and/or prophylactic treatment. The treatment includes the diminishment or alleviation of at least one symptom associated or caused by interstitial cystitis. For example, treatment can be diminishment of one or several symptoms of interstitial cystitis or complete eradication of it.

The invention is further explained by the following examples.

EXAMPLES

Example 1

Rat and Mouse Models of Interstitial Cystitis

In this Example, a number of different agents with or without 5ASA were tested in a rat model of Interstitial Cystitis. In addition to 1% N,O carboxymethychitosan (NOCC) solution, NSNOCC(N-succinyl-NOCC) and sNOCC (sulfonated NOCC) were also tested.

Materials and Methods

Animals: Female Sprague-Dawley rats (225-250 g) were purchased from Charles River Laboratories. Animals were provided with food and water ad libitum.

Intra-vesicular inoculation of protamine sulfate (PS) and LPS: Rats were anesthetized and a lubricated sterile catheter (PE-50) was inserted under sterile conditions as described above. The catheter was connected to a 1 ml syringe via a 25 G needle and the bladder was emptied as described above. One group of rats was inoculated with 1 ml PS (10 mg/ml) in phosphate buffered saline (PBS) into the bladder via the catheter. After 45 minutes, the bladders were emptied, washed with PBS, then given a second treatment with 1 ml LPS (750 µg/ml) in PBS for 30 minutes. During the treatment period, the catheters were occluded to prevent loss of the solution in the bladder and then removed at the end of the last treatment.

For the first study, rats were sacrificed at various times after inoculation and the bladders were removed and fixed in 10% formalin for histology. Sections were cut and stained with hematoxylin and eosin. Sections were examined for inflammation in a blinded manner. In the second study, the test agent was administered, in a volume of 1 ml, 1 day after the PS/LPS treatment. The animals were sacrificed 4 days later (i.e. 5 days post inoculation).

Results

Efficacy of Chitinous Polymers

Various chitinous polymers were tested for efficacy in reducing the inflammatory score. The agents were delivered 1 day after the PS/LPS treatment and no further treatment of the animals was performed. Animals were sacrificed on day 5 post inoculation.

Control rats received only saline as a post-inoculation treatment. The saline control in this experiment is a positive control for inflammation since these animals were treated with PS/LPS but received only saline after the inflammatory stimulus.

When 5ASA was used, the 5ASA was heat sterilized then mixed with the sterile chitinous derivative in an aseptic environment (laminar flow hood). In one group, the 5ASA had been chemically bound to the NSNOCC before delivery to the laboratory (NSNOCC-5ASA). This was either used by itself or mixed with 5ASA in a similar manner to the other compounds. In the latter case, the compound is referred to as NSNOCC-5ASA+5ASA to denote the fact that the compound has 5ASA covalently bound to the NSNOCC as well as mixed in with the NSNOCC solution.

Three chitinous polymers were tested in this experiment: the NSNOCC referred to above; the NSNOCC-5ASA referred to above; and 1% sNOCC (sulfated NOCC). The sNOCC was used in combination with 5ASA in this experiment.

The bladders were prepared for histological examination. The five point scale described above was used to calculate a total inflammatory score and a mean inflammatory score. The mean inflammatory scores are shown in Table 2.

TABLE 2

| Group | Mean Inflammatory Score |
| --- | --- |
| saline (control) | 11.7 |
| NSNOCC | 10.3 |
| NSNOCC + 5ASA | 10.3 |
| NSNOCC − 5ASA + 5ASA | 10.0 |
| NOCC + 5ASA | 9.8 |
| sNOCC + 5ASA | 6.0 |

Discussion and Conclusions

The data show that some reduction in inflammation is seen in all of the groups treated with chitinous polymers when compared to control. The 1% sNOCC+ASA showed the largest reduction and thus was selected for further study. This example demonstrates that the rat PS/LPS model of IC yielded substantial bladder inflammation and that chitinous polymers have shown promise as agents to reduce the inflammation.

Example 2

Efficacy of sNOCC in Reducing Inflammation in a Rat Model of Interstitial Cystitis Materials and Methods Animals: Female Sprague-Dawley rats (225-250 g) were purchased from Charles River Laboratories. Animals were provided with food and water ad libitum.

Intra-vesicular inoculation of protamine sulfate (PS) and LPS: Rats were anesthetized with sodium pentobarbital (65 mg/kg). The surface area around the urethral opening was swabbed with 70% isopropyl alcohol and Betadine. A lubricated sterile catheter (PE-50), handled with sterile gloves, was inserted into the bladder through the urethral opening. The catheter was connected to a 1 ml syringe via a 25 G needle and the bladder was emptied as described above. One group of rats was inoculated with 1 ml PS (10 mg/ml) in phosphate buffered saline (PBS) into the bladder via the catheter. After 45 minutes, the bladders were emptied, washed with PBS, then given a second treatment with 1 ml LPS (750 µg/ml) in PBS for 30 minutes. During the treatment period, the catheters were occluded to prevent loss of the solution in the bladder and then removed at the end of the last treatment.

Treatment with the test agents and assessment: After PS/LPS inoculation, rats were randomized into the various groups. One day after PS/LPS inoculation, the test agent was administered in a volume of 1 ml. The animals were sacrificed 4 days later (i.e. five days post inoculation) and urine was collected for determination of levels of the inflammatory cytokine TNF-α. The bladders were then removed and fixed in 10% formalin for histology. Sections were cut and stained with hematoxylin and eosin. Sections were examined for inflammation in a blinded manner.

The parameters of inflammation measured were: increased venous blood vessel size and volume (venous congestion), edema, cellular infiltration, and epithelial damage. These parameters are all characteristic of acute inflammation. The parameters were measured by a blinded observer using a five point score with 0 being the least severe and 5 being the most severe. A total inflammatory score was calculated for each rat by adding together the scores of the four inflammatory parameters. A mean total inflammatory score was calculated for each group.

For TNF assessment, urine from all animals in each group was pooled. The urine was stored at −70° C. until all the animals had been sacrificed so that all the urine could be tested at one time. Urine was diluted 1/10 with assay diluent and ELISA performed using standard protocols. The amount of TNF in each sample was ascertained by comparing the absorbance to a standard curve of various concentrations of recombinant rat TNF.

Statistical analysis: Statistical analysis included the one way ANOVA and the Fisher's multiple comparison test for comparing among groups. These analyses were used for multiple comparisons among groups. For direct comparisons between two groups, the Two Sample t test was used and a p value of <0.05 was considered significant.

Results

Inflammation Scores: Table 1 shows the mean severity of inflammation and the percent reduction from control.

TABLE 1

| Group | Mean Inflammatory Score (±SEM) | % reduction of inflammation from saline treated control |
|---|---|---|
| saline (control) | 12.7 (±1.5) | n/a |
| 1% HA | 9.5 (±1.0) | 25.0 |
| saline + 5ASA | 7.9 (±1.8) | 37.5 |
| 1% sNOCC | 7.0 (±1.2) | 44.8 |
| 1% sNOCC + 5ASA | 7.7 (±1.4) | 39.2 |
| 3% sNOCC + 5ASA | 3.2 (±0.8) | 74.9 |

These data show that 3% sNOCC+5-ASA is very effective at reducing the mean inflammatory score. This formulation reduced the severity by 74.9% when compared to the saline control. This group was significantly different from all other groups by the Fisher's multiple comparison test and was highly significantly different from the saline (PBS) control when directly compared by the t test ($p<0.001$).

It is also notable that 1% sNOCC by itself also showed considerable efficacy. This formulation reduced the mean severity score by 44.8% when compared to control. This difference was also significant by the Fisher's multiple comparison test. There was no apparent benefit to the addition of 5ASA to the 1% sNOCC. No statistically significant difference in the total inflammatory score was recorded between 1% sNOCC and 1% sNOCC+5ASA when compared directly ($p=0.7$).

It was also found that 1% hyaluronic acid (HA) did not significantly reduce inflammation. Although a 25% decrease in inflammation was calculated, the variance in the groups was such that this was not statistically significant by the Fisher's multiple comparison test. It should also be noted that in four of the slides from the 1% HA treatment group, blood in the bladder or hemorrhage in the bladder tissue was found. None of the other groups showed these aspects of pathology, including the phosphate buffered saline (PBS) treatment control.

Assessment of TNF in the urine: TNF is a cytokine closely associated with sites of inflammation. The level of TNF in the urine has been found to correlate with the extent of inflammation in the bladder. The fact that the TNF levels are lowest in the 3% sNOCC+5ASA group correlates well with the observations of low inflammatory scores in this group. This formulation showed a highly significant reduction in TNF levels when compared to the other groups as measured by ANOVA and Fisher's multiple comparison test and when compared directly to the saline (PBS) control group by the t test ($p=0.006$). Likewise, both the 1% sNOCC and the 1% sNOCC+5ASA showed significant reductions in TNF levels. In contrast to the inflammatory scores, the addition of 5ASA to the 1% sNOCC further reduced the TNF levels. The difference between these two groups was found to be significant by the t test ($p=0.013$)

The results of assessment of TNF levels in the urine of the rats in the different treatment groups are shown in FIG. 1. FIG. 1 shows that 1% sNOCC, 1% sNOCC+5ASA, and 3% sNOCC+5ASA were most effective in reducing TNF-α production in rat urine.

The foregoing examples are merely exemplary and those skilled in the art will be able to determine other modifications to the described procedures which fall within the scope of the invention. Accordingly, the invention is defined by the following claims and equivalents thereof.

What is claimed is:

1. A method for treating a disorder in a mucosal tissue selected from the group consisting of interstitial cystitis, Crohn's disease, inflammatory bowel disease and colitis comprising topically administering a medicament containing an effective amount of a sulfated chitinous polymer including subunits of the formula:

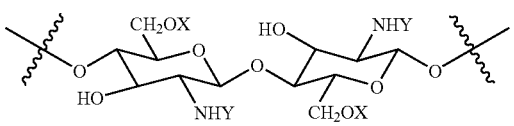

wherein

X is independently selected from hydrogen, $SO_3^-B$, $-(CH_2)_bCOG$, or $-(CH_2)_bCOOZ$ for each occurrence;

Y is independently selected from $SO_3^-B$, $-C(=O)-R-CO_2Z$, $-C(=O)-R-COG$, hydrogen, carboxyalkyl, or a pharmaceutically acceptable salt thereof for each occurrence, provided that at least 1% of Y groups and/or 1% of X groups on said polymer are $SO_3^-B$;

R is independently selected from the group consisting of alkyl, alkenyl, and aryl;

b is 1-5;

B is hydrogen or a cation;

G is 5-aminosalicylic acid or a pharmaceutically acceptable salt thereof; and

Z is hydrogen, a cation, is 5-aminosalicylic acid, or a pharmaceutically acceptable salt thereof.

2. The method of claim 1, wherein at least 10% of said X groups on said polymer are $-(CH_2)_bCOG$, or $-(CH_2)_bCOOZ$.

3. The method of claim 1, wherein at least 10% of said Y groups on said polymer are $SO_3^-B$.

4. The method of claim 1, wherein b is 1.

5. The method of claim 1, wherein R is $-(CH_2)_a-$, wherein a is 1-8.

6. The method of claim 5, wherein a is 2, 3, or 4.

7. The method of claim 1, wherein said sulfated chitinous polymer is selected from the group consisting of N-sulfated N,O-carboxymethylchitosan; N-sulfated O-carboxymethylchitosan; N-sulfated N,O-carboxyethylchitosan; N-sulfated O-carboxymethylchitosan; N-sulfated N,O-carboxypropylchitosan; N-sulfated O-carboxypropylchitosan; sulfated chitosan and combinations thereof.

8. The method of claim 1, wherein said pharmaceutically acceptable carrier is suitable for administration via catheter or enema.

9. The method of claim 1, wherein said sulfated chitinous polymer is administered at a concentration of about 0.5% to about 30% of the total weight of the composition.

10. The method of claim 9, wherein said sulfated chitinous polymer is administered at a concentration of about 1.0% to about 10% of the total weight of the composition.

11. The method of claim 1, wherein said subject is a human.

12. The method of claim 1, wherein the medicament is administered after a surgical operation.

13. A pharmaceutical composition, acceptable for administration via catheter or enema, comprising a sulfated chitinous polymer and a pharmaceutically acceptable carrier, said sulfated chitinous polymer including subunits of the formula:

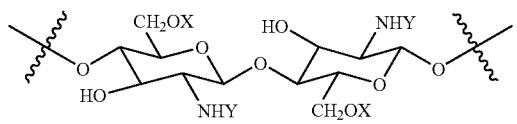

wherein

X is independently selected from hydrogen, $SO_3^-B$, $-(CH_2)_bCOG$, or $-(CH_2)_bCOOZ$ for each occurrence, provided that at least 10% of X groups on said polymer are $-(CH_2)_bCOOZ$ or $-(CH_2)_bCOG$;

Y is independently selected from $SO_3^-B$, $-C(=O)-R-CO_2Z$, $-C(=O)-R-COG$, hydrogen, carboxyalkyl, or a pharmaceutically acceptable salt thereof for each occurrence, provided that at least 1% of Y groups and/or 1% of X groups on said polymer are $SO_3^-B$;

R is independently selected from the group consisting of alkyl, alkenyl, and aryl;

b is 1-5;

B is hydrogen or a cation;

G is 5-aminosalicylic acid or a pharmaceutically acceptable salt thereof; and

Z is hydrogen, a cation, 5-aminosalicylic acid, or a pharmaceutically acceptable salt thereof, and wherein said sulfated chitinous polymer is selected from the group consisting of N-sulfated N,O-carboxymethylchitosan; N-sulfated O-carboxymethylchitosan; N-sulfated N,O-carboxyethylchitosan; N-sulfated O-carboxyethylchitosan; N-sulfated N,O-carboxypropylchitosan; N-sulfated O-carboxypropylchitosan; and combinations thereof.

14. The pharmaceutical composition of claim 13, wherein at least 10% of said Y groups on said polymer are $SO_3^-B$.

* * * * *